United States Patent
Zauser et al.

[11] Patent Number: 5,855,853
[45] Date of Patent: Jan. 5, 1999

[54] PETRI DISH HOLDER

[75] Inventors: Kurt Zauser; Thomas Zauser, both of Kernen, Germany

[73] Assignee: Orgamed Laborsysteme Vertriebsgesellschaft mbH, Kernen, Germany

[21] Appl. No.: 860,938

[22] PCT Filed: Jan. 5, 1996

[86] PCT No.: PCT/EP96/00029

§ 371 Date: Jul. 15, 1997

§ 102(e) Date: Jul. 15, 1997

[87] PCT Pub. No.: WO96/23055

PCT Pub. Date: Aug. 1, 1996

[30] Foreign Application Priority Data

Jan. 27, 1995 [DE] Germany .................. 195 02 520.2

[51] Int. Cl.⁶ .................................................. B65D 85/62
[52] U.S. Cl. .......................................... 422/104; 435/809
[58] Field of Search ............................. 435/305.1, 305.2, 435/305.3, 288.3, 809; 422/102, 104; 206/445

[56] References Cited

U.S. PATENT DOCUMENTS

| | | |
|---|---|---|
| 3,562,114 | 2/1971 | Steidl et al. . |
| 4,012,288 | 3/1977 | Lyman et al. . |
| 4,143,765 | 3/1979 | Moss, III . |
| 4,287,155 | 9/1981 | Tersteeg et al. . |
| 4,321,330 | 3/1982 | Baker et al. . |
| 5,747,333 | 5/1998 | Jungmann-Campello et al. .... 422/104 |

FOREIGN PATENT DOCUMENTS

| | | |
|---|---|---|
| 0290018A2 | 11/1988 | European Pat. Off. . |
| 0447893 | 9/1991 | European Pat. Off. . |
| 4313807A1 | 11/1993 | Germany . |
| 4300231C1 | 12/1993 | Germany . |
| 62-269757 | 11/1987 | Japan . |

OTHER PUBLICATIONS

Fisher Scientific Catalog, 1983, p.293.
Patent Abstracts of Japan, vol. 12, No. 155 (C–494), 12 May 1988, 62–269757, (Hitachi Electronics Eng Co Ltd.).
Catalogue Sigma—Aldrich Techware, p. 356, Laboratory Equipment and Supplies, 1995–1996.

*Primary Examiner*—Jeffrey Snay
*Attorney, Agent, or Firm*—Jones, Tullar & Cooper, P.C.

[57] ABSTRACT

In a holder for Petri dishes with a basic support at least partially surrounding the Petri dishes, the latter are secured against falling out of the basic support because said basic support has a substantially C-shaped cross-section and the Petri dishes are surrounded to the extent of over 180° around their circumference.

18 Claims, 3 Drawing Sheets

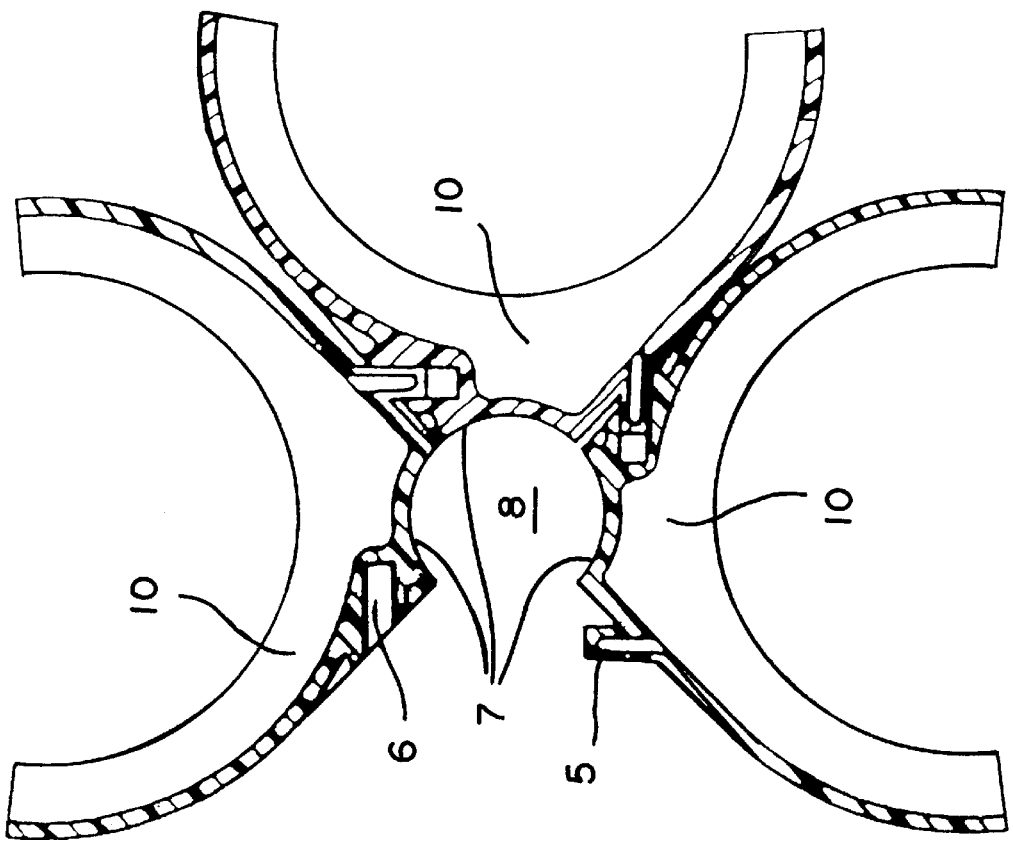
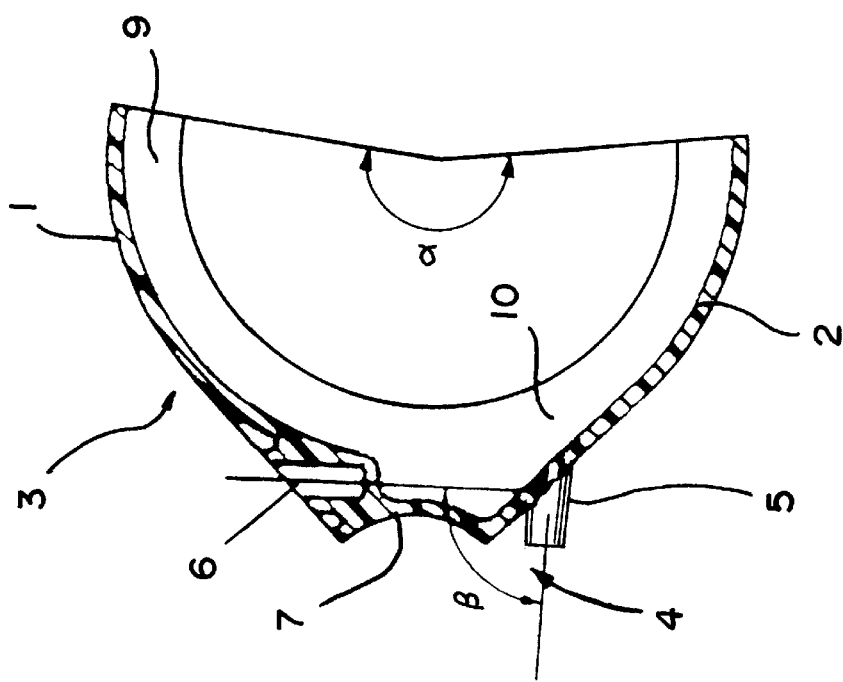

PETRI DISH HOLDER

BACKGROUND OF THE INVENTION

The present invention relates to a petri dish holder, having a basic support that grips the petri dishes on at least part of their circumference.

BACKGROUND OF ART

As a rule, petri dishes are flat plastic dishes with a cover and are used for instance for growing and incubating bacteria and fungus cultures. These cultures are not grown in merely a single petri dish but rather in many such petri dishes, and a number of tests are performed on the cultures in a predetermined order. An important factor is that a predetermined order be adhered to during the entire test procedure, which can take several days. In this time, the petri dishes must be moved constantly back and forth between the incubator and the workspaces, and care must be taken to adhere to the order of the petri dishes, which are typically stacked one above the other. When they are carried about, it is never possible to carry more than only a few of the loosely stacked petri dishes without risk. Since the identification of the dishes is not visible during the entire test procedure, major organizational effort must be expended to keep the individual petri dishes, which as a rule have run through different cycles, in the predetermined workspace-dictated order. Particularly whenever fractions need special treatment for further tests, the risk is great that individual petri dishes will be mistaken for one another. Mistakes can slip into the test results in this way. Another major risk is that despite careful handling, the stacked petri dishes can fall over and contaminate the counters or the floor with pathogenic bacteria.

From German Patent DE 43 00 231 C1, petri dishes have been disclosed that are equipped with a special connection unit, so that on the one hand they can be inserted one above the other and on the other can be clamped in a holder and can also be swiveled out of their connection. A disadvantage of these petri dishes has proved that their design is extremely complicated, and even in mass production these petri dishes are therefore relatively expensive.

German Published Patent Application DE 26 28 344 A1 has disclosed a tray for receiving a plurality of petri dishes. Although the petri dishes are retained in a way secure against loss here, nevertheless this tray can hold only a very small number of petri dishes, which are moreover inconvenient to remove from the tray.

European Published Patent Application EP 447 893 A2 has disclosed a holding system for a stack of petri dishes, with which while the stack can be held without difficulty, removing individual petri dishes from the stack is possible, if at all, only with great difficulty.

SUMMARY OF THE INVENTION

It is therefore an object of the invention to furnish a holder for petri dishes that on the one hand holds a large number of such dishes and on the other in which individual dishes or the entire stack can be removed from the holder without difficulty, and moreover the holder is relatively inexpensive and offers protection so that the dishes will not fall out.

In a holder of the type referred to at the outset, this object is attained in accordance with the present invention in that the basic support is embodied with an essentially C-shaped cross section and grips one or more petri dishes, stacked one above the other, over an angle of more than 180° of their circumference.

The essentially C-shaped design has the particular advantage that one or more petri dishes (with covers) can be easily thrust radially into this holder, without having to make special provisions on the holder for retaining or securing the dishes. Above all, this holder need not be either opened or closed, nor must the holder be taken apart or put back together again in order to receive the dishes. In the apparatus of the present invention, a single dish, but as a rule a stack of 21 petri dishes, is thrust all at once radially into the basic support and is circumferentially gripped by it and retained. The circumference of the petri dishes is circumferentially gripped and gripped slightly from behind over an angle of 182° to 220°, preferably over an angle of 190°. This gripping from behind on the one hand prevents the petri dishes from falling out of the holder and on the other hand makes it easy to carry the holder about with the dishes inserted in it.

In this way, high security against transposition of individual petri dishes is created, so that the order in which the individual bacterial cultures are tested can be adhered to effortlessly and without particular organizational provisions. The entire stack can be removed from the holder in a single operation, and this stack, after being processed, can be reinserted in the same order of the dishes into the holder, so that the petri dishes are secured again against slipping, being transposed, and the like. The stack of dishes can also be processed as follows: The uppermost dish is removed, and after work is ended it is inserted inverted, that is, with its underside facing upward or its top side facing downward, into a new holder. The next dish, after work on it is completed, is likewise placed inverted into the new holder on top of the previously inserted dish. Once the stack has all been processed, the completely filled holder is inverted, and the new stack is now again in the correct position. The holder also, by the extensive circumferential gripping of the petri dishes, offers good protection against breakage and toward avoiding contamination.

In an especially preferred embodiment, the basic support, on the side remote from the side that receives the petri dish or petri dishes, has a connecting device for coupling together one or more further holders. Via this connecting device, the basic supports can be joined together into a holder unit, the holding unit receiving a corresponding multiple number of petri dishes. In this way, up to 84 petri dishes, for instance, can be carried about and stored without risk, using the holder unit.

In an especially preferred embodiment, the connecting device is a peg and hole connection. However, a tongue and groove connection, such as a dovetail connection, is also conceivable. This peg and hole connection makes it possible to take the holder unit apart into the individual holders (for instance for cleaning purposes) and then to reassemble it without tools. The two connecting elements of the connecting device may be at an angle of 0°, 60°, 90°, 108°, etc., to one another. Thus 2, 3, 4, 5 or more holders can be joined together to make a single holder unit. The holders can be joined together and detached from one another either with or without petri dishes inserted.

In a preferred embodiment, the joined-together holders form a receptacle for a stand or the like. This receptacle provides a cylindrical recess, for instance, into which a vertical rod of a turntable can be inserted. In this way, the holder unit, with the petri dishes provided inside it, can easily be worked with at the work space, with whichever side is to be used being retrieved by turning the entire unit.

A further feature provides that two or more such holders can be stacked one above the other. This can multiply the holding capacity of the entire holder unit. The space required at the work spaces is reduced considerably in this way, while the petri dishes are held as securely as before.

To prevent the petri dishes from axially slipping out of the holder, the holder is provided with a base and/or a cover.

The material from which the holder is made has the property of being at least slightly elastic. Moreover, the material of the holder is temperature-resistant, so that the petri dishes can be placed together with the holder in an incubator. To enable easy cleaning and disinfection of the holder, the material is temperature resistant up to at least 150° C, and is resistant to acids, lyes, alcohols, and other disinfectants. In any case, the material should readily withstand a temperature of 125° C over a period of approximately 25 minutes, for instance in an autoclave.

Moreover, the material can be dyed or has certain colors or codes. The color identification of the individual holders makes it possible to identify individual stages in the work or progress in the testing of the cultures. In this way it is immediately apparent what work steps have already been performed on the cultures and what the next steps to be performed are. To that end, the petri dishes are taken out of the one holder having the one colored identification and are placed, after the work step has been performed, in a holder that has a correspondingly different coloration or identification.

In another embodiment, the holder can be written on, so that the particular stage in the testing can be identified on the holder. This writing can easily be removed again. In other embodiments it is provided that the holder has an identification field, on which markings, notices or the like can be secured.

To make transporting the holder easy and problem-free, the holder has a carrying device, or a carrying device can be secured to the holder. A simple version provides bail-like carrying handles.

Other advantages of the present invention are that the holder has a symmetrical structure with respect to its center plane orthogonal to the longitudinal axis. In this way the holder can be inverted without difficulty and used further. Moreover, all the basic supports are embodied identically, which has the advantage of needing only a single injection molding tool. The individual basic supports are also each embodied in one piece.

Further advantages, characteristics and details of the invention will become apparent from the ensuing description, in which especially preferred exemplary embodiments are described in detail, in conjunction with the drawing. The characteristics shown in the drawing and recited in the specification and the claims can each be essential to the present invention either individually or in arbitrary combination with one another.

BRIEF DESCRIPTION OF THE DRAWINGS

FIG. 1, is a cross section through a holder in accordance with a preferred embodiment of the present invention;

FIG. 2, shows a plurality of holders joined together;

DESCRIPTION OF THE PREFERRED EMBODIMENT

Figure 3:
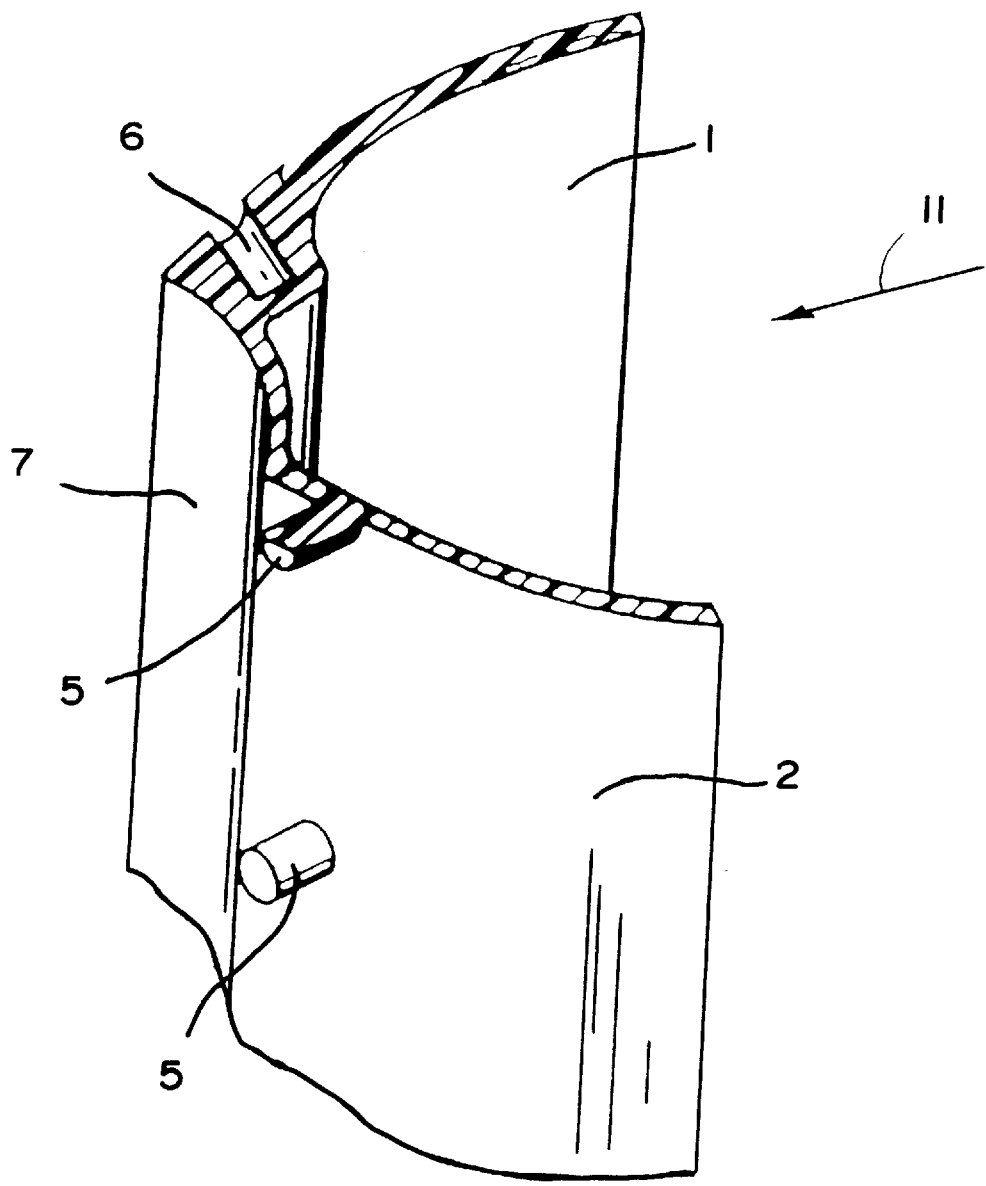
FIG. 3, is a perspective view of the holder of FIG. 1.

FIG. 1 shows a cross section through one embodiment, in cross section, of the holder according to the present invention, which is embodied substantially in the shape of a C. The two legs 1 and 2 of the basic support 3 form an angle α of 190°. This allows one or more petri dishes, not shown, to be securely gripped from behind, the petri dishes having an outer diameter that is substantially equivalent to the inside diameter of the arc-shaped legs 1 and 2. On their ends facing one another, the legs 1 and 2 form a connecting device 4, by way of which four holders can be joined together to make one holder unit. The connecting device 4 has a peg 5 and a bore 6, and the axes of the peg 5 and the bore 6 are at an angle β of 90° from one another. In this way, the peg 5 can be joined to a bore 6 of an adjacent holder, and the peg of another adjacent holder can be joined to the bore 6. This arrangement is shown in FIG. 2. From FIG. 2 it can also be seen that the connecting device 4 has a recess 7, which together with further recesses 7 of adjacent holders (a total of four of them) forms a receptacle 8, for instance for a vertical rod of a turntable.

It can also be seen from FIGS. 1 and 2 that the insides of the legs 1 and 2 are provided with a radially inward-protruding edge 9, which forms a base 10 for petri dishes inserted into the holder and prevents the petri dishes from falling out in the axial direction.

FIG. 3 shows a fragmentary perspective view of the holder of FIG. 1; it is clearly apparent that an entire stack of petri dishes can conveniently be inserted radially into this holder, that is, in the direction of the arrow 11, or removed from the holder counter in the direction of the arrow 11. The inserted stack is engaged slightly from behind by the free ends of the legs 1 and 2 of the holder and is thus restrained against falling out radially. To securely join together a plurality of such holders to form a holder unit, a plurality of pegs 5 and bores 6, totalling six each, are placed one above the other. In this way, the individual holders are securely joined together over their entire length.

Figure 4:
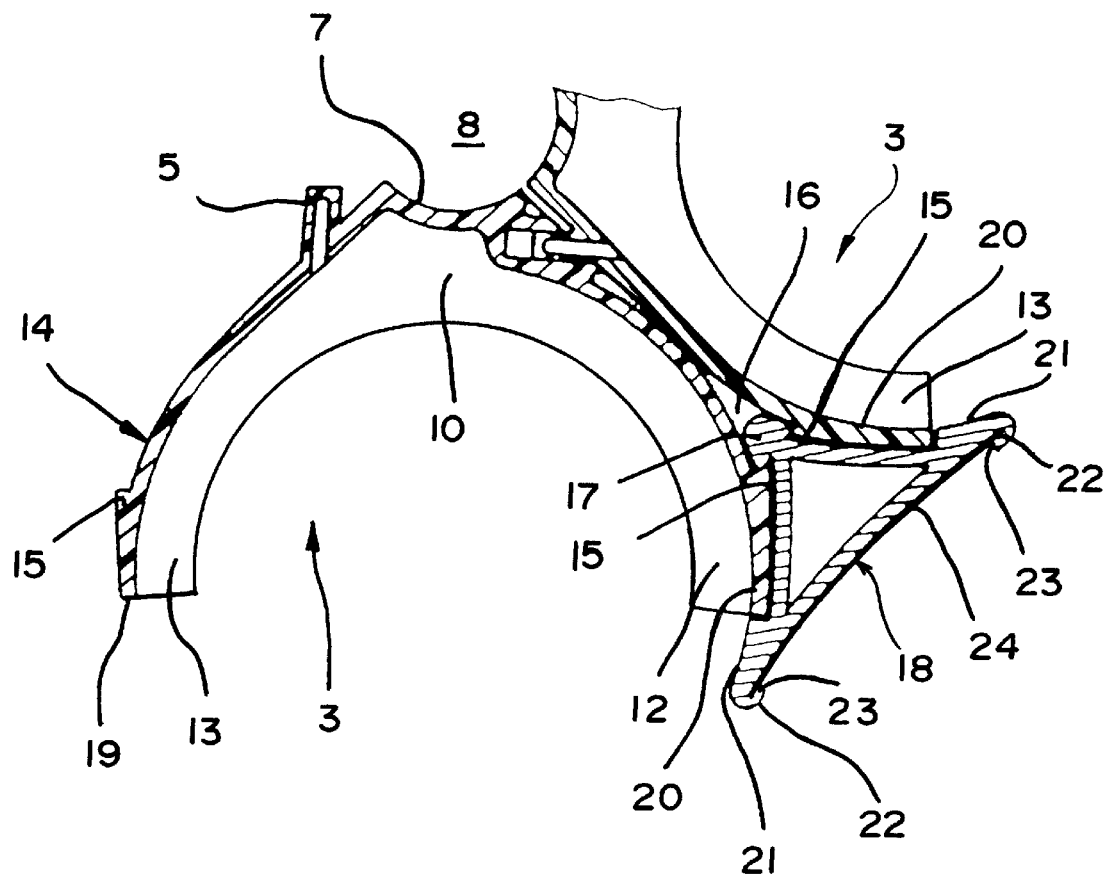
FIG. 4, is a fragmentary section through another embodiment of the holder with an inserted corner element.

In FIG. 4, a variant of the holder is shown, in which the free ends 12 and 13 of the basic supports 3 are provided with retaining arms 15 on their outsides 14. Two retaining protrusions 15 facing one another, of two basic supports 3 form a detent receptacle 16 for a detent protrusion 17 of a corner element 18.

This corner element 18 may extent over part or all of the height of the holder. It has a substantially triangular shape and is formed such that it conforms to the outsides 15 of the basic supports 3. It engages and extends past the end face 14 of the free ends 12, 13 of the basic supports, so that the inside face 20, against which the petri dishes rest, is lengthened by an extension 21. The corner element 18 is hollow, which increases its elasticity. The extensions 21 create the possibility of securely receiving even petri dishes of smaller diameter, since they increase wrap angle, for instance to 210°. Moreover, the outer ends 22 of the corner element have slitlike recesses 23 into which a card 24 or the like that can be written on can be inserted.

We claim:

1. A holder for petri dishes, having a basic support for gripping at least part of the circumference of the petri dishes, said support being embodied to have an essentially C-shaped cross section and adapted to grip one or more petri dishes, stacked one above the other, over an angle (α) of more than 180° of their circumference, wherein said basic support on a side remote from the side that receives the petri dish or petri dishes, has a connecting device for coupling together one or more further holders.

2. The holder of claim 1, wherein the angle (α) is in the range from 182° to 200°.

3. The holder of claim 1, wherein said connecting device is a peg and hole connection.

4. The holder of claim 1, wherein said connecting device is a tongue and groove connection.

5. The holder of claim 1, wherein said connecting device comprises two connecting elements which are at an angle (β) of 0°, 60°, 90° or 108°, to one another.

6. The holder of claim 1, wherein 21 petri dishes stacked one above the other are insertable into the holder.

7. The holder of claim 1, wherein when coupled together with at least one further holder, the sides having said connecting devices cooperate to a receptacle for a stand.

8. The holder of claim 7, wherein said receptacle is formed by a cylindrical recess.

9. The holder of claim 7, wherein said stand has a vertical rod and optionally a turntable.

10. The holder of claim 1, wherein it is stackable with additional such holders in the axial direction.

11. The holder of claim 1, wherein it is provided with a base and/or a cover.

12. The holder of claim 1, wherein it is made from plastic or metal.

13. The holder of claim 1, wherein it is formed by a material which is temperature-resistant up to 150° C.

14. The holder of claim 1, wherein it is formed of a material which can be dyed or has selected colors or codes.

15. The holder of claim 1, wherein it can be written on.

16. The holder of claim 1, wherein it has an identification filed.

17. The holder of claim 1, wherein it has a carrying device, or a carrying device can be secured to the holder.

18. A holder unit, comprising two or more holders as defined in claim 1.

* * * * *